(12) United States Patent
Shor et al.

(10) Patent No.: US 11,259,996 B2
(45) Date of Patent: *Mar. 1, 2022

(54) SYSTEMS, DEVICES, AND METHODS OF MAKING AND USING PTFE DENTAL PLUGS

(71) Applicants: Alexander Shor, Mercer Island, WA (US); Jimmy Janakievski, Tacoma, WA (US)

(72) Inventors: Alexander Shor, Mercer Island, WA (US); Jimmy Janakievski, Tacoma, WA (US)

( * ) Notice: Subject to any disclaimer, the term of this patent is extended or adjusted under 35 U.S.C. 154(b) by 366 days.

This patent is subject to a terminal disclaimer.

(21) Appl. No.: 16/250,982

(22) Filed: Jan. 17, 2019

(65) Prior Publication Data

US 2019/0151206 A1 May 23, 2019

Related U.S. Application Data

(62) Division of application No. 15/085,820, filed on Mar. 30, 2016, now Pat. No. 10,182,974.

(51) Int. Cl.
| *A61C 8/00* | (2006.01) |
| *A61K 6/887* | (2020.01) |
| *A61K 6/19* | (2020.01) |
| *A61C 5/00* | (2017.01) |
| *C08F 114/26* | (2006.01) |

(52) U.S. Cl.
CPC ............... *A61K 6/887* (2020.01); *A61C 5/00* (2013.01); *A61C 8/0048* (2013.01); *A61C 8/0065* (2013.01); *A61C 8/0068* (2013.01); *A61K 6/19* (2020.01); *C08F 114/26* (2013.01)

(58) Field of Classification Search
CPC ......... A61C 5/00; A61C 8/0048; A61C 8/065; A61C 8/0068; A61C 8/0057; C08F 114/26; A61K 6/19
See application file for complete search history.

(56) References Cited

U.S. PATENT DOCUMENTS

| 5,032,445 | A | 7/1991 | Scantlebury et al. |
| 5,064,373 | A | 11/1991 | Staubli et al. |
| 5,116,226 | A | 5/1992 | Linkow |
| 2003/0212372 | A1 | 11/2003 | Bills et al. |
| 2007/0207186 | A1 | 9/2007 | Scanlon et al. |
| 2007/0259315 | A1 | 11/2007 | Last-Pollak |
| 2010/0098737 | A1* | 4/2010 | Darby ............ A61L 27/54 424/423 |
| 2015/0017603 | A1 | 1/2015 | Antonini et al. |

FOREIGN PATENT DOCUMENTS

KR 20-2014-0005818 U 11/2014

* cited by examiner

*Primary Examiner* — Heidi M Eide
(74) *Attorney, Agent, or Firm* — Seed Intellectual Property Law Group LLP

(57) ABSTRACT

A method of using a dental filler is disclosed. The method may include securing a prosthetic to a dental implant, the prosthetic having an access channel therethrough. The method may also include filling a portion of the access channel by inserting a polytetrafluoroethylene dental plug into the access channel and compressing the polytetrafluoroethylene dental plug within the access channel.

8 Claims, 9 Drawing Sheets

SYSTEMS, DEVICES, AND METHODS OF MAKING AND USING PTFE DENTAL PLUGS

BACKGROUND

Technical Field

The present disclosure generally relates to systems, devices, and methods of filling and sealing access channels of abutments, crowns, bridges, and bars. More particularly, some embodiments herein relate to PTFE dental plugs and systems and methods of using such plugs in filling and sealing access channels of abutments, crowns, bridges, bars and natural teeth.

Description of the Related Art

Dental implant supported restoration devices are used for the replacement of missing teeth. A dental implant supported restoration device includes a dental implant anchored in the bone and a prosthetic secured to the dental implant. Prosthetics, such as abutments, crowns, bridges and bars can be attached to the dental implants via a retaining screw.

When attaching prosthetics to a dental implant using a screw, an access channel to allow insertion and stabilization of the prosthetic screw is formed in the prosthetic. The access channel is then sealed off from the oral environment with a seal to prevent collection of foreign debris and foreign bodies within the access channel and to minimize growth of microorganisms.

Cotton has been used to fill access channels, but cotton is easily compressible, hydrophilic, organic, and porous, with many voids. Cotton fill material does not provide sufficient stiffness to support the seal, and leads to seal breakage which then results in fluid intrusion into the access channel and growth of microorganisms supported by the cotton within the access channel.

Common plumber's tape has also been used to fill the access channel. Such thin tape material is folded or crumpled into the access channel, and when filling the access channel it is still compressible. The folded and crumpled nature of the tape, when used to fill access channels, still provides inadequate support for the access channel seal, and the folds and crumples in the tape can collect water and foreign debris that supports microorganism growth. Such tape also suffers from unknown degradation and transformation during sterilization and possible contamination, including incorporation of perfluorooctanoic acid.

BRIEF SUMMARY

A method of using a dental filler is disclosed. The method may include securing a prosthetic to a dental implant, the prosthetic having an access channel therethrough. The method may also include filling a portion of the access channel by inserting a polytetrafluoroethylene dental plug into the access channel and compressing the polytetrafluoroethylene dental plug within the access channel.

A dental filler system is disclosed. The dental filler system may include a polytetrafluoroethylene dental plug having a first length and a first diameter. The dental filler system may also include a dental prosthetic having an access channel formed therein, the access channel having a second diameter that is larger than the first diameter, having a fill length that is smaller than the first length, and being shaped to receive a fastener.

A dental filler is disclosed. The dental filler may include a body of polytetrafluoroethylene material extending from a first end to a second end and having a first cross-sectional area at the first end and a second cross-sectional area at the second end. The body may a volumetric density between 0.15 and 2.15 g/cm$^3$ and a low crystallinity characterized by a crystalline to amorphous peak melt temperature between 320 and 340 degrees C.

DETAILED DESCRIPTION

Figure 1A:
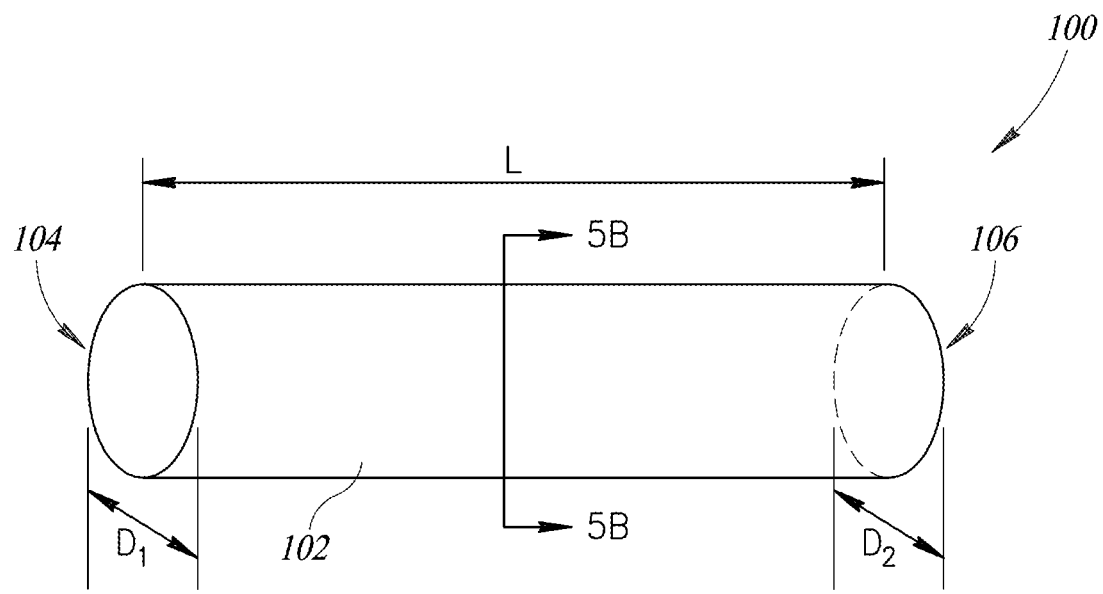
FIG. 1A depicts a pre-cut length of PTFE plug according to one or more embodiments disclosed herein.
Figure 1B:
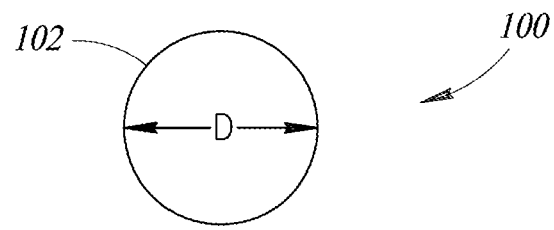
FIG. 1B depicts a cross section of the PTFE plug of FIG. 1A according to one or more embodiments disclosed herein.

FIGS. 1A and 1B show an embodiment of a PTFE access channel plug 100. The PTFE access channel plug 100 shown in FIG. 1A includes a body 102 that extends between a first end 104 and a second end 106. The body 102 may be made from material, including virgin PTFE (polytetrafluoroethylene) resin, that is perfluorooctanoic acid (PFOA) free. In some embodiments, the material that forms the body 102 is 100% virgin PTFE resin. In other embodiments, the material that forms the body 102 may be less than 100% virgin PTFE resin.

PTFE is a synthetic fluoropolymer of tetrafluoroethylene, which has a high molecular weight and includes carbon and fluorine. The high bond strength between carbon and fluorine makes the material hydrophobic and nonreactive to most harsh chemicals. The PTFE plug 100 may have a volume density of between 0.15 g/cm³ and 2.15 g/cm³, and more preferably between 0.15 g/cm³ and 0.75 g/cm³. The PTFE plug 100 may also include single axis or bi-axially expanded PTFE. In some embodiments, the PTFE plug 100 may include a combination of one or more of single axis and bi-axially expanded PTFE. Expanded PTFE may have a volume density range between 0.2-1.4 g/cm³ which correlates to an air volume between 90-35%.

The volume density of the PTFE plug is one factor that determines how the PTFE plug compresses and fills the cavity or access channel. In some embodiments, volume densities of 0.25 g/cm³, 0.50 g/cm³, and 0.75 g/cm³ may be used.

The PTFE plug 100 may include PTFE material with a low crystallinity. For example, the PTFE material may have a differential scanning calorimetry reported at greater than 340° C. peak melt temperature. In some embodiments, the PTFE material may have a differential scanning calorimetry reported at between 320° C.-350° C. peak melt temperature. Low crystallinity PTFE material facilitates the creep and compressive abilities of the PTFE material in the PTFE plug 100, which aids in filling voids and asymmetrical features within an access channel or cavity.

In some embodiments, the PTFE material is either a porous PTFE material or a nonporous PTFE material. A porous PTFE material, particularly low density, porous PTFE material, provides more flexibility in filling cavities and access channels within a cavity or prosthetic, because the low density, porous PTFE material is more compressible and flexible, thus allowing the PTFE material to be more easily packed into a cavity or prosthetic during a dental procedure.

The combination of volume densities between 0.15 g/cm³ and 2.15 g/cm³, porous PTFE material compression, and a low crystallinity aids in more completely filling the volume of a cavity or access channel within a tooth or prosthetic and results in removing the air from within an access channel or cavity. By more completely filling the volume of a cavity or access channel and removing more air from the access channel or cavity, voids where microorganisms may grow are avoided and any gases that may be beneficial to the growth of microorganisms are removed from the cavity or access channel; thus growth of microorganisms is inhibited or significantly reduced as compared to using cotton, plumbers tape, or other packing material susceptible to forming voids within an access channel or cavity.

The body of the PTFE plug 100 may also include an anti-bacterial material to aid in inhibiting microbial growth in the access channel in which the PTFE plug 100 is inserted and to also aid in inhibiting microbial growth in or on the PTFE plug 100. In some embodiments, the PTFE plug 100 may be impregnated or coated with anti-bacterial coatings, filling, or solutions.

As shown in FIG. 1A, the PTFE plug 100 may have a particular length L between the first end 104 of the PTFE plug 100 and the second end 106 of the PTFE plug 100. For example, the length L may be between 5 mm and 10 mm. In some embodiments, the length L may be up to 35 mm. The length L may be selected as the length suitable to fill a cavity or access channel within a tooth or prosthetic, as discussed later.

Figure 9A:
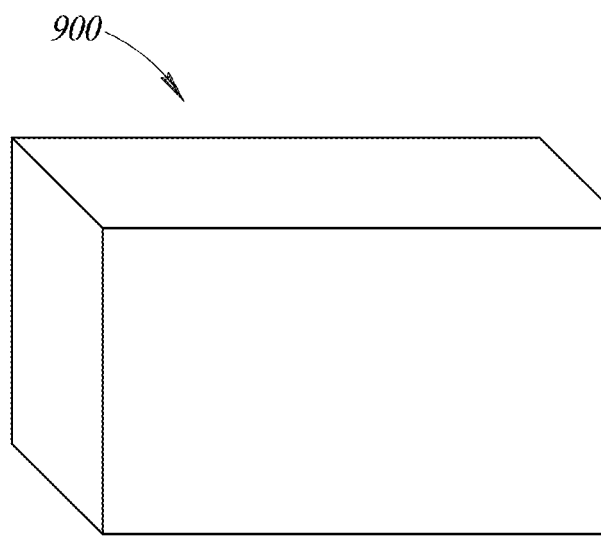
FIG. 9A depicts a PTFE fill material with a quadrilateral cross section according to one or more embodiments disclosed herein.
Figure 9B:
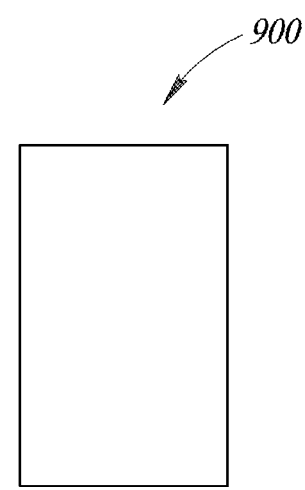
FIG. 9B depicts a cross section of the PTFE fill material with the quadrilateral cross section of FIG. 8A according to one or more embodiments disclosed herein.
Figure 10A:
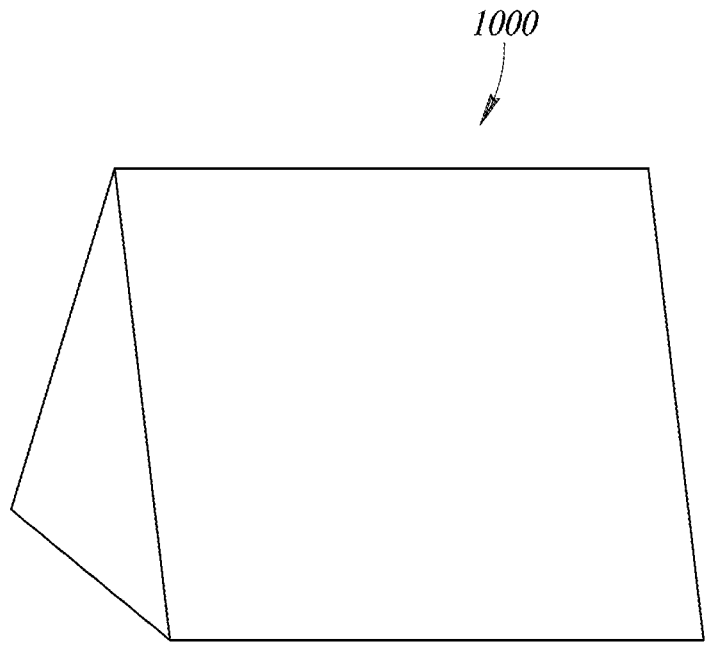
FIG. 10A depicts a PTFE fill material with a triangular cross section according to one or more embodiments disclosed herein.
Figure 10B:
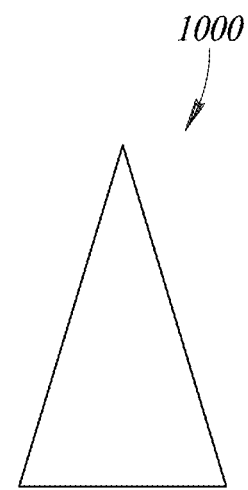
FIG. 10B depicts a cross section of the PTFE fill material with the triangular cross section of FIG. 10A according to one or more embodiments disclosed herein.
Figure 11A:
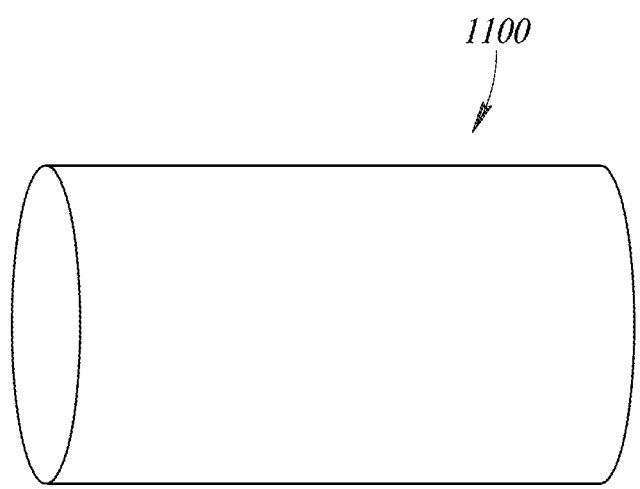
FIG. 11A depicts a PTFE fill material with an oval cross section according to one or more embodiments disclosed herein.
Figure 11B:
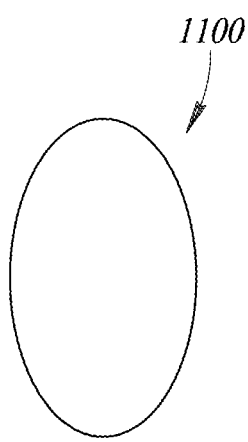
FIG. 11B depicts a cross section of the PTFE fill material with the oval cross section of FIG. 11A according to one or more embodiments disclosed herein.

The PTFE plug 100 has a circular cross section with a constant diameter along its length L. A round cross-section is suitable for filling cavities or access channels. In some embodiments, the PTFE plug 100 may have other cross-sectional shapes. For example, the PTFE plug 100 may have a quadrilateral shape such as a square or rectangle, as shown by PTFE plug 900 in FIGS. 9A and 9B; an oval shape, as shown by PTFE plug 1100 in FIGS. 11A and 11B; a triangular shape, as shown by PTFE plug 1000 in FIGS. 10A and 10B; or other shape suitable for filling cavities and access channels within a tooth or prosthetic. These various cross-sectional shapes can aid in more completely filing portions of an access channel, for example, when an access channel is drilled within the tooth, it may not be round. In such cases an oval shape or another shaped PTFE plug may be more suitable for use in filling the cavity than a round PTFE plug.

In some embodiments, the PTFE plug 100 may be formed from a braid of several PTFE filaments in a manner similar to that of a rope.

Figure 8:
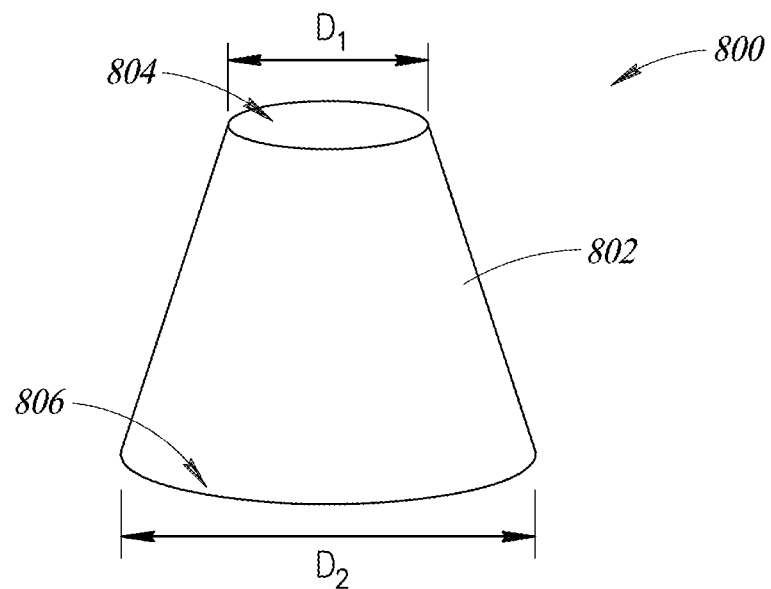
FIG. 8 depicts a tapered PTFE fill material according to one or more embodiments disclosed herein.

In some embodiments, the diameter of the PTFE plug 100 may vary. For example, as shown in FIG. 1A, the PTFE plug 100 has a first diameter $D_1$ at the first end 104 and a second diameter $D_2$ at the second end 106. Such variations in diameter may facilitate filling access channels or cavities that have varying cross-section along their depth. One such example of a PTFE plug having a varying diameter along its length is shown in FIG. 8, where a PTFE plug 800 has a first diameter $D_1$ at the first end 804 and a second diameter $D_2$ at the second end 806, wherein the first diameter $D_1$ is smaller than the second diameter $D_2$ which gives a body 802 of the PTFE plug 800 a cone shape that is tapered. Other shapes, such as square shapes and oval shapes, may not be defined by a diameter, but they may have a varying cross-sectional area along their length such that they taper from one end of the PTFE plug to an opposing end of the PTFE plug.

Figure 7:
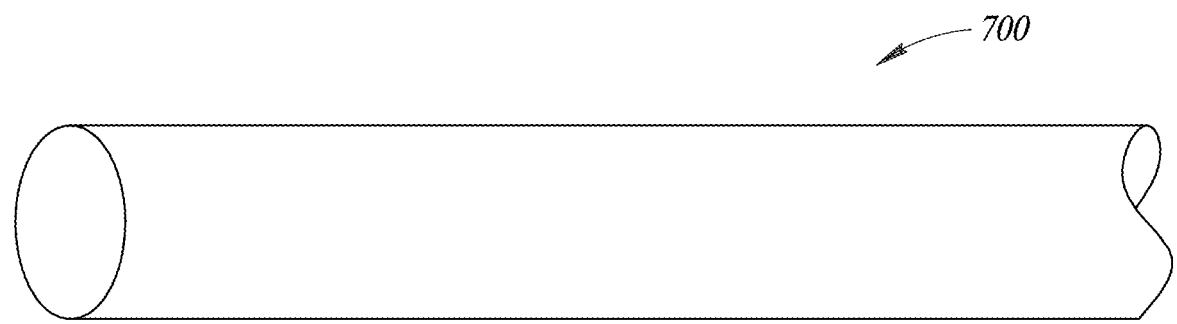
FIG. 7 depicts an elongated PTFE fill material according to one or more embodiments disclosed herein.

In some embodiments, the PTFE plug may be dispensed from a continuous length of PTFE material; for example, as shown in FIG. 7, a continuous length of PTFE filament may be provided. The continuous length of PTFE filament is not an infinite length of PTFE material, instead it is a length of material in excess of the length to fill a single cavity or access channel. For example, the PTFE filament 700 shown in FIG. 7 may be cut into several PTFE plugs for use in filling several access channels.

Referring back to FIGS. 1A and 1B, the PTFE plug 100 or the PTFE filament 700 may have a constant diameter D of between approximately 0.040 inches and approximately 0.16 inches, such that the first diameter $D_1$ and the second diameter $D_2$ are the same.

In some embodiments, the PTFE filament 700 may have a first diameter that is less than the diameter of an access channel, such as access channel 214 of FIG. 1 and a length that is greater than the length of the access channel 214. In some embodiments, the length of the PTFE filament 700 that is used to fill an access channel or cavity, such as access channel 214, is many times longer than the length of the access channel.

The various shapes of PTFE plugs, and filaments 100, 700, 800 900, 1000, 1100, can reduce the time a dentist or oral surgeon spends during a procedure. For example, when a dentist or oral surgeon has a PTFE plug 100 that has a shape, length L, and diameter or cross-sectional area that is particularly suited to a particular cavity or access channel within a prosthetic, then the dentist or oral surgeon spends less time preparing and packing fill material during the procedure, which may reduce the total time of procedure. For example, in some embodiments, the diameter of the PTFE plug may be less than the diameter of the cavity or access channel. When the a dentist or dental surgeon compresses the PTFE plug within the cavity or access channel, the diameter of the PTFE plug increases and the outer surface of the PTFE plug expands and contacts the inner surface of the cavity or access channel.

In some embodiments, the diameter of the PTFE plug may be greater than the diameter of the cavity or access channel. When the a dentist or dental surgeon compresses the PTFE plug within the cavity or access channel, the diameter of the PTFE plug shrinks to conform to the inner surface of the cavity or access channel.

Figure 2:
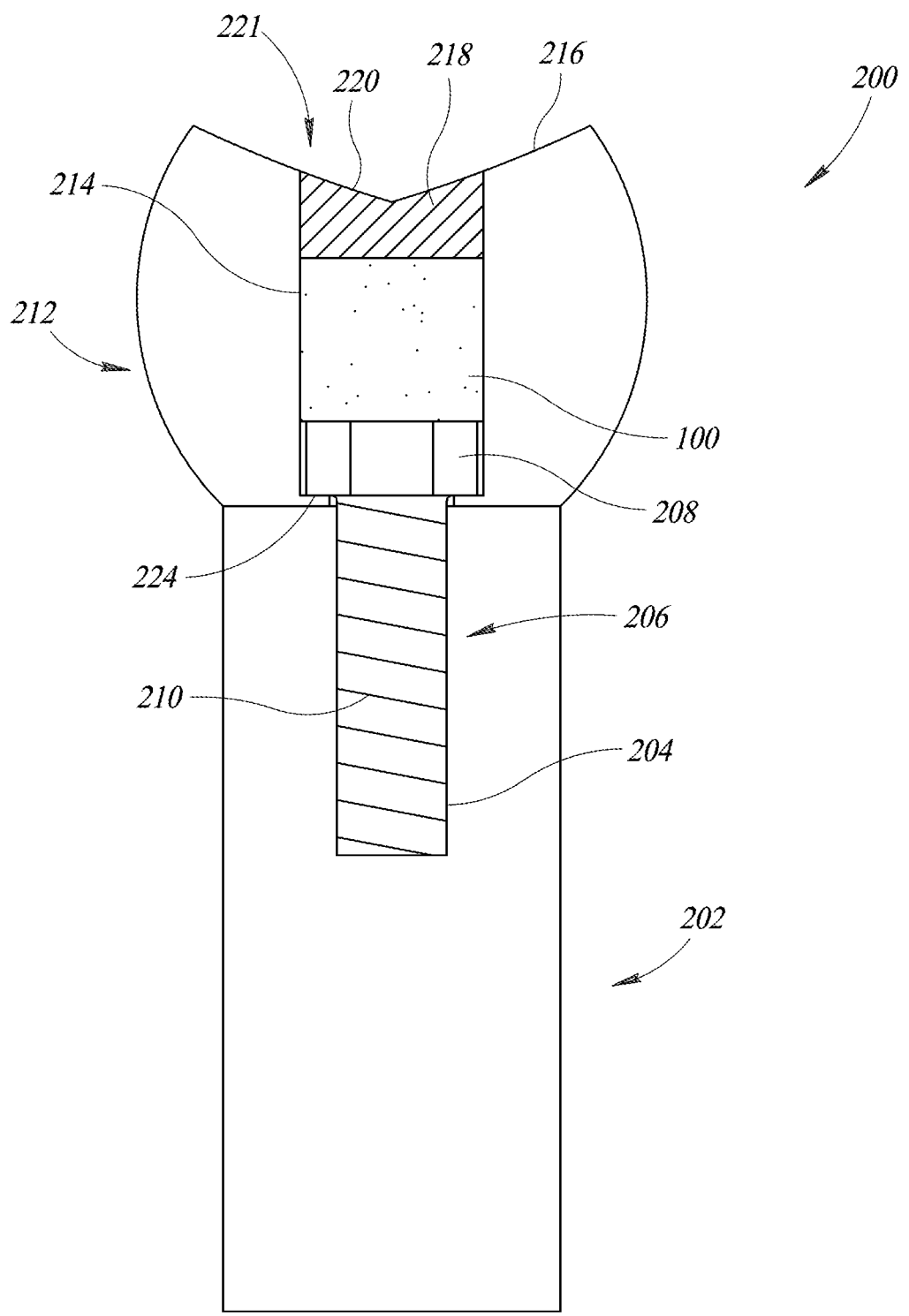
FIG. 2 depicts an implant supported one-piece restoration according to one or more embodiments disclosed herein.

FIG. 2 shows an embodiment of a dental implant system 200. The dental implant system 200 includes a dental implant 202, a prosthetic 212, and a fastener 206 that attaches the prosthetic 212 to the implant 202. The fastener 206 attaches the prosthetic 212 to the implant 202 when the threads 210 of the fastener 206 engage with the sidewalls of the threaded hole 204 of the implant 202 and the head 208 of the fastener 206 clamps the flange 224 of the prosthetic 212 to the implant 202.

The prosthetic 212 includes an access channel 214 for receiving the fastener 206. After the fastener is inserted into the access channel 214 and has secured the prosthetic 212 to the implant 202, the head 208 of the fastener 206 substantially fills a bottom portion of the access channel 214. The middle portion of the access channel 214 is filled with the PTFE plug 100 and compressed to fill the voids within the access channel to provide support for an overlaying polymer filling material 218.

The top portion of the access channel 214 is then sealed with the overlaying polymer filling material 218. The polymer filling material 218 includes an outer surface 220 that, combined with an outer surface 216 of the prosthetic, forms a working or biting surface 221 of the prosthetic 212.

As shown in FIG. 2, the PTFE plug 100 fills the access channel 214 and, after the polymer filling material 218 is formed, the access channel 214 is sealed off and devoid of voids and air that would otherwise provide for growth of microorganisms within the access channel 214.

Figure 3:
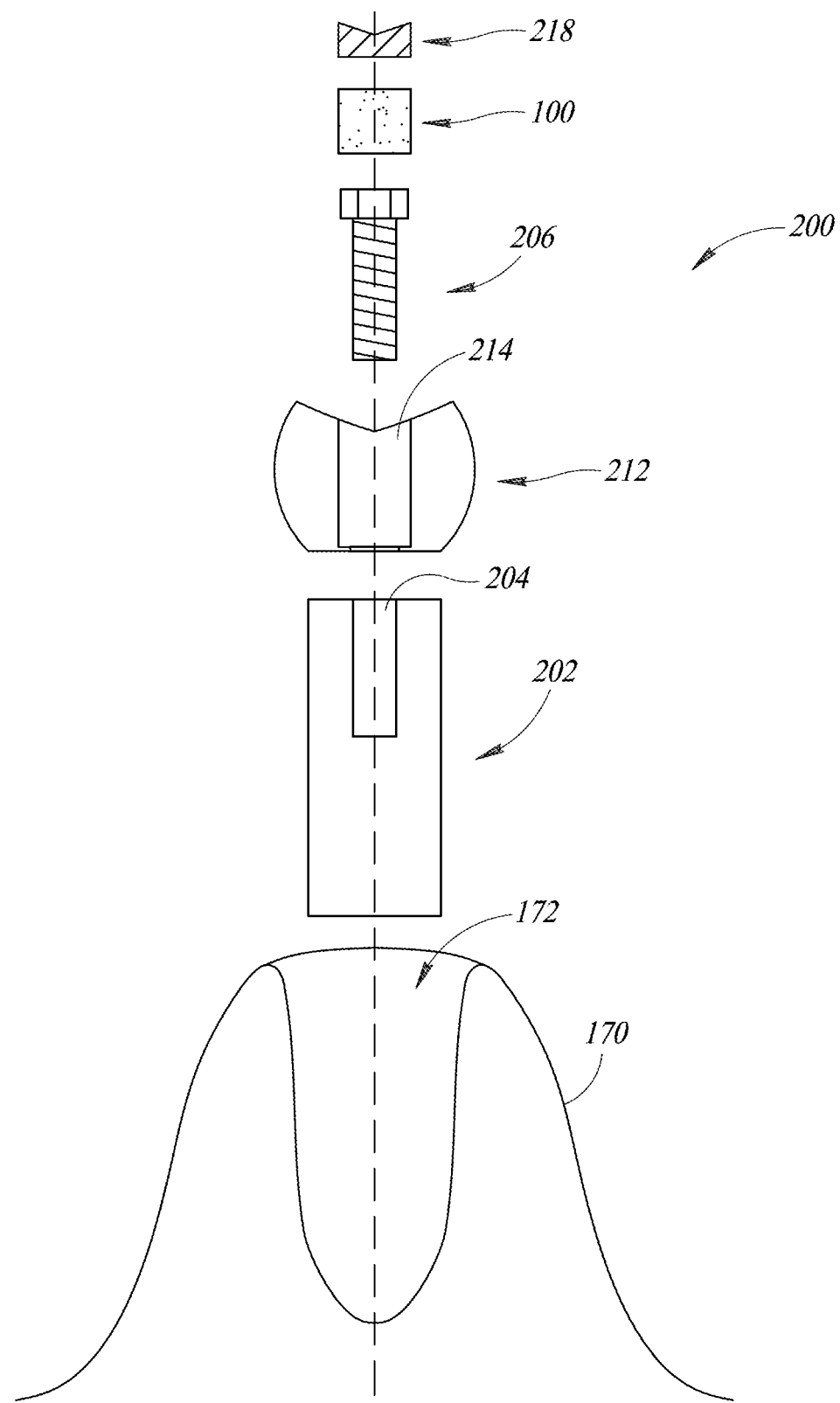
FIG. 3 depicts an exploded view of the implant supported one-piece restoration according to one or more embodiments disclosed herein.

FIG. 3 depicts an exploded view of the dental implant system 200 shown in FIG. 2. To install the dental implant system 200 into a patient, a cavity 172 is formed in a jawbone 170 of a patient. The cavity 172 may be formed by the removal of a tooth or by other means such as surgically forming the cavity 172 within the jawbone 170. In some embodiments, the implant 202 may form the cavity 172 within the jawbone 170.

The implant 202 is then inserted into and secured within the cavity 172. After the implant 202 is secured within the cavity 172, the prosthetic 212 is secured to the implant 202 by inserting the fastener 206 into the access channel 214 and then into a threaded hole 204 of the implant 202. As the fastener is screwed into the implant 202, the head 208 of the fastener 206 clamps the prosthetic 212 to the implant 202.

With the prosthetic 212 secured to the implant 202, the access channel 214 is then filled with the PTFE plug 100 and compressed to fill the voids within the access channel to provide support for the overlaying polymer filling material 218.

The PTFE plug may have a predetermined size and shape based on the shape of the access channel 214 within the prosthetic 212. In some embodiments, the PTFE plug 100 may have a size and shape, and in particular a length and diameter (or cross-sectional area), that is selected based on the shape and volume of the access channel 212 that is filled by the PTFE plug 100. For example, a dentist or dental surgeon may be provided with a prosthetic 212 having an access channel 214 of a known size along with a fastener 206 also being a known size. By knowing the size of the fastener 206 or a part of the fastener, such as the head 208, and in particular the volume or amount the fastener 206 will occupy within the known size of the access channel 214, a PTFE plug 100 of a predetermined size and shape may be provided to the dentist or dental surgeon for use in filling the access channel 214.

In some embodiments, the dentist or oral surgeon selects a PTFE plug 100 of a particular size and shape during the procedure. In some embodiments, the dentist or oral surgeon selects a PTFE filament of a particular diameter or cross-sectional area and shape and cuts the PTFE filament to a length appropriate for filling a portion of the access channel 214 while leaving an appropriate portion of the access channel 214 open for the polymer filling material 218.

In some embodiments, the PTFE plug 100 may be multiple PTFE plugs 100, each sized and shaped to fill a portion of the access channel 214.

After the PTFE plug 100 is placed and compacted within the access channel 214, the polymer filling material 218 is used to fill the remaining portion of the access channel 214 and to seal the access channel 214 from an environment external to the access channel 214.

In some embodiments, for example when using a PTFE filament 700, a PTFE plug is formed by inserting the PTFE filament 700 into the access channel 214 and compacting the PTFE filament 700 into the access channel 214.

In such embodiments, the PTFE filament 700 has a diameter less than the diameter of the access channel 214 and a length that is greater, sometimes many times greater, for example, 3-5 times greater than the length of the access channel 214. To form the PTFE plug within the access channel 214, a dentist inserts an end of the PTFE filament 700 into the access channel 214 and then proceeds to push additional length of PTFE filament 700 into the access channel 214. This may cause the PTFE filament 700 to fold over itself and deform inside the access channel 214 until the PTFE filament 700 has deformed to fill the access channel 214.

Figure 4:
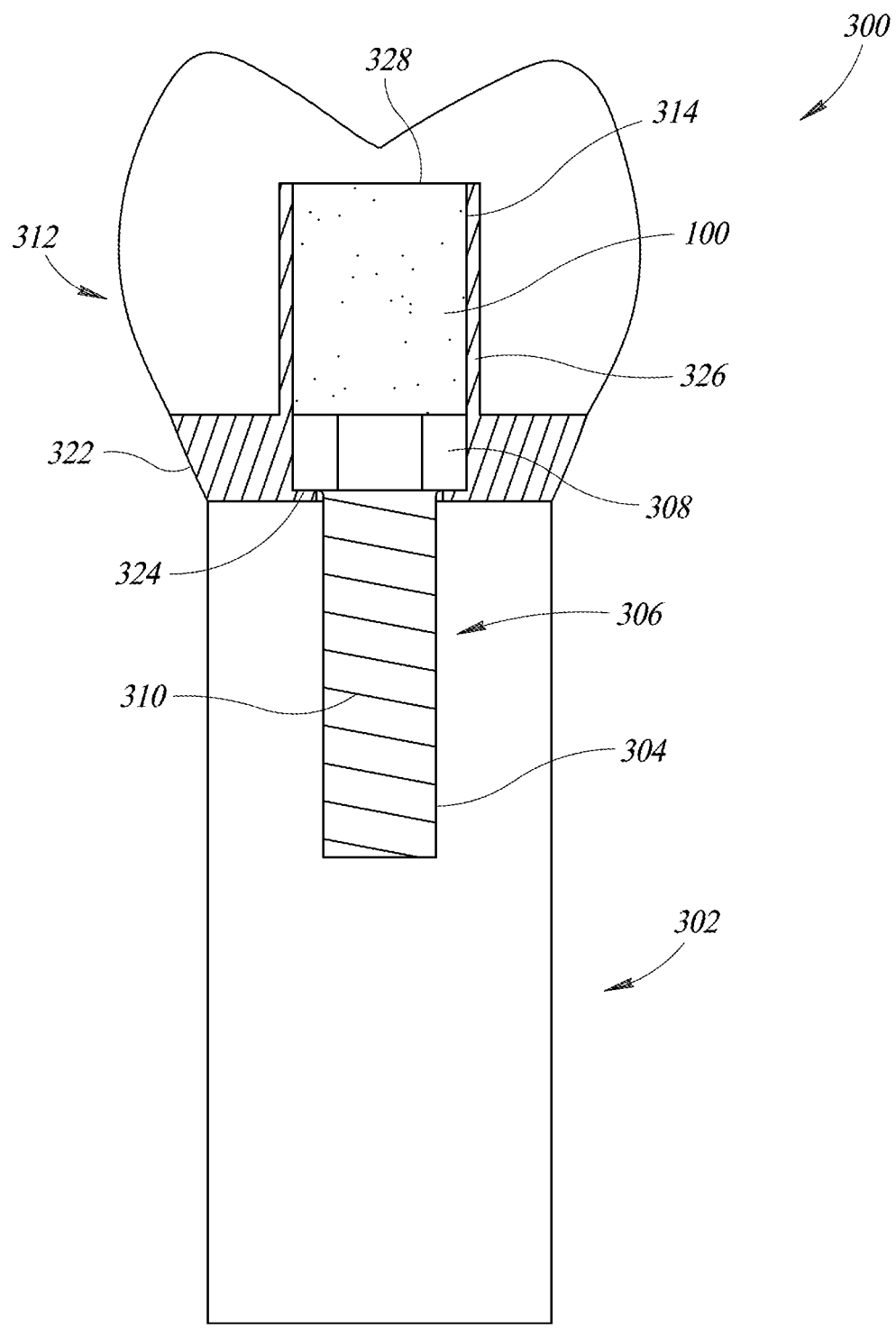
FIG. 4 depicts an abutment supported restoration according to one or more embodiments disclosed herein.

FIG. 4 shows an embodiment of a dental implant system 300. The dental implant system 300 includes a dental implant 302, a prosthetic 312, an abutment 322, and a fastener 306 that attaches the abutment 322 to the implant 302. The fastener 306 attaches the abutment 322 to the implant 302 when the threads 310 of the fastener 306 engage with the sidewalls of the threaded hole 304 of the implant 302 and the head 308 of the fastener 306 clamps the flange 324 of the abutment 322 to the implant 302.

The abutment 322 includes an access channel 314 for receiving the fastener 306. The access channel is formed by a hollow cylindrical extension 326 that extends from a base of the abutment 322. After the fastener 306 is inserted into the access channel 314 and has secured the abutment 322 to the implant 302, the head 308 of the fastener 306 substantially fills a bottom portion of the access channel 314. The top portion of the access channel 314 is filled with the PTFE plug 100.

After the PTFE plug 100 is placed and compacted into the access channel 314, the access channel 314 is then capped and sealed off by the prosthetic 312 that is placed over the abutment 322. The prosthetic 312 includes a channel 328 that is sized and shaped to mate with an exterior surface of the extension 326.

As shown in FIG. 3, after placement of the prosthetic 312, the PTFE plug 100 fills the access channel 314, resulting in the access channel 314 being devoid of voids and air that would otherwise provide for growth of microorganisms within the access channel 314.

To install the dental implant system 300 into a patient, a cavity is formed in the jaw bone of a patient. The implant 302 is then inserted into and secured within the cavity. After the implant 302 is secured within the cavity, the abutment 322 is secured to the implant 302 by inserting the fastener 306 into the access hole channel 314 and then into the threaded hole 304 of the implant 302. As the fastener is screwed into the implant 302, the head 308 of the fastener 306 clamps the abutment 322 to the implant 302.

With the abutment 322 secured to the implant 302, the access channel 314 is then filled with the PTFE plug 100, the prosthetic 312 is secured to the abutment 322, and the access channel 314 is sealed. The PTFE plug 100 may have a predetermined size and shape based on the shape of the access channel 314 within the abutment 322. In some embodiments, the PTFE plug 100 may have a size and shape, and in particular a length and diameter, that is selected based on the shape and volume of the access channel 312 that is filled by the PTFE plug 100. For example, a dentist or dental surgeon may be provided with an abutment 322 having an access channel 314 of a known size along with the fastener 306 also being a known size By knowing the size of the fastener 306 or a part of the fastener, such as the head 308, and in particular the volume or amount the fastener 306 will occupy within the known size of the access channel 314, a PTFE plug 100 of a predetermined size and shape may be provided to the dentist or dental surgeon for use in filling the access channel 314.

Figure 5:
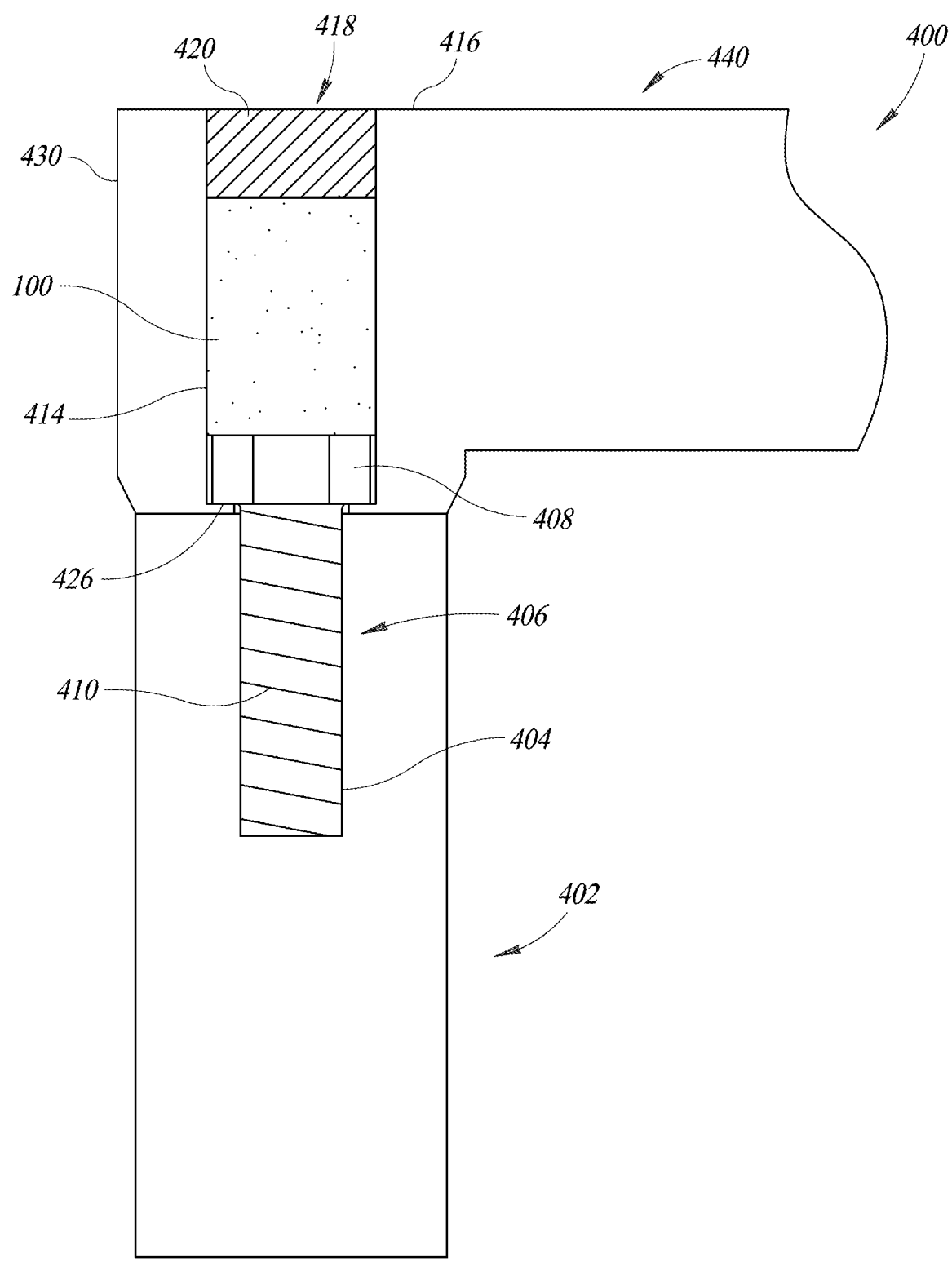
FIG. 5 depicts an implant supported bar restoration according to one or more embodiments disclosed herein.

FIG. 5 shows an embodiment of a dental implant supported bar system 400. The system 400 includes a dental implant 402, an implant supported bar 440 and a fastener 406 that attaches the implant supported bar 440 to the implant 402. The fastener 406 attaches the implant supported bar 440 to the implant 402 when the threads 410 of the fastener 406 engage with the sidewalls of the threaded hole 404 of the implant 402 and the head 408 of the fastener 406 clamps the flange 426 of the implant supported bar 440 to the implant 202.

The implant supported bar 440 includes an access channel 414 for receiving the fastener 406. After the fastener is inserted into the access channel 414 and has secured the supported bar 440 to the implant 402, the head 408 of the fastener 406 substantially fills a bottom portion of the access channel 414. The middle portion of the access channel 414 is filled with the PTFE plug 100 and the top portion of the access channel 414 is sealed with an overlaying polymer filling material 418. The polymer filling material 418 includes an outer surface 420 that is co-planer with the outer surface 416 of the implant supported bar 440.

As shown in FIG. 5, the PTFE plug 100 fills the access channel 414 and, after the polymer filling material 418 is formed, the access channel 414 is sealed off from the external environment and devoid of voids and air that would otherwise provide for growth of microorganisms within the access channel 414.

To install the system 400 into a patient, a cavity is formed in the jaw bone of a patient. The cavity may be formed by the removal of a tooth or by other means such as surgically forming the cavity within the jaw bone. The implant 402 is then inserted into and secured within the cavity. After the implant 402 is secured within the cavity, the implant supported bar 440 is secured to the implant 402 by inserting the fastener 406 into the access hole channel 414 and then into the threaded hole 404 of the implant 402. As the fastener is screwed into the implant 402, the head 408 of the fastener 406 clamps the implant supported bar 440 to the implant 402.

With the implant supported bar 440 secured to the implant 402, the access channel 414 is then filled with the PTFE plug 100 and polymer filling material 418. The PTFE plug may have a predetermined size and shape based on the shape of the access channel 414 within the implant supported bar 440. In some embodiments, the PTFE plug 100 may have a size and shape, and in particular a length and diameter, that is selected based on the shape and volume of the access channel 414 that is filled by the PTFE plug 100. For example, a dentist or dental surgeon may be provided with an implant supported bar having an access channel 414 of a known size along with a fastener 406 also of a known size. By knowing the size of the fastener 406 or a part of the fastener, such as the head 408, and in particular the volume or amount the fastener 406 will occupy within the known size of the access channel 414, a PTFE plug of a predetermined size and shape may be provided to the dentist or dental surgeon for use in filling the access channel 414.

After the PTFE plug 100 is placed and compacted within the access channel 414, the polymer filling material 418 is used to fill the remaining portion of the access channel 414 and to seal the access channel 414 from an environment external to the access channel 414.

Figure 6:
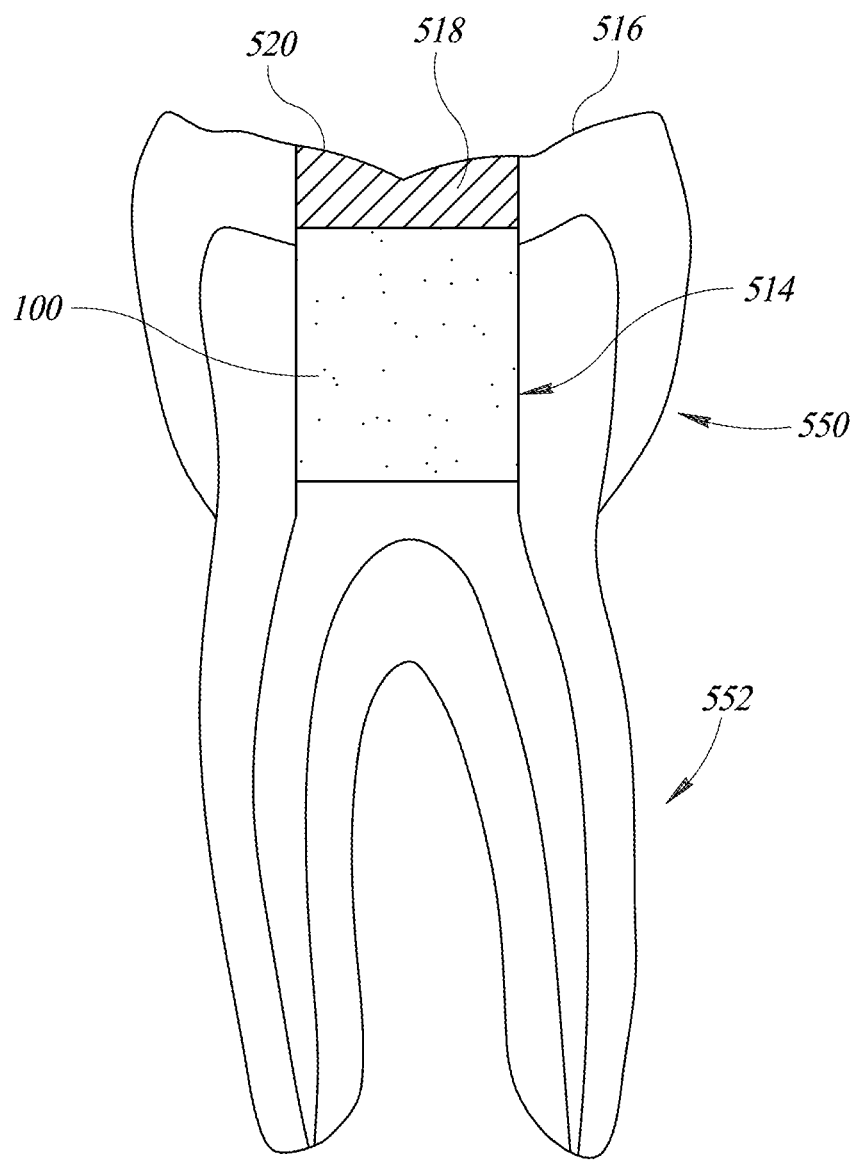
FIG. 6 depicts a root canal treated tooth restoration according to one or more embodiments disclosed herein.

FIG. 6 shows an embodiment of a tooth 550 having a filled and sealed access channel 514. In a root canal procedure, an access channel 514 is formed in the tooth 550, so that a dentist or dental surgeon can gain access to the interior of the roots 552 of the tooth 550. After the dentist or dental surgeon has completed their work on the tooth, a portion of the access channel 514 is filled with the PTFE plug 100 and the top portion of the access channel 514 are sealed with an overlaying polymer filling material 518. The polymer filling material 518 includes an outer surface 520 that, combined with the outer surface 516 of the tooth 550, forms a working or biting surface of the tooth 550.

As shown in FIG. 5, the PTFE plug 100 fills the access channel 514 and, after the polymer filling material 518 is formed, the access channel 514 is devoid of voids and air that would otherwise provide for growth of microorganisms within the access channel 514.

U.S. patent application Ser. No. 15/085,820, filed Mar. 30, 2016, is hereby incorporated herein by reference in its entirety.

The various embodiments described above can be combined to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A dental filler system comprising:
a dental filler including a body of polytetrafluoroethylene material extending from a first end to a second end, the dental filler having a first cross-sectional area at the first end, a second cross-sectional area at the second end, and an anti-bacterial material; and
a dental prosthetic including an access channel having a third cross-sectional area larger than the first and second cross-sectional areas;
wherein the dental filler is configured to be positioned within the access channel and to be compressed within the access channel to increase the first and second cross-sectional areas of the dental filler while the dental filler is within the access channel.

2. The dental filler system of claim 1, wherein:
the first cross-sectional area is greater than the second cross-sectional area.

3. The dental filler system of claim 1, wherein:
the first cross-sectional area is the same as the second cross-sectional area.

4. The dental filler system of claim 1 wherein the anti-bacterial material is on an external surface of the body.

5. The dental filler system of claim 1 wherein the body is impregnated with the anti-bacterial material.

6. The dental filler system of claim 1, wherein:
the body has a length extending between the first end and the second end; and
the length corresponds to a depth of the access channel.

7. The dental filler system of claim 1, wherein the body has a circular cross section.

8. The dental filler system of claim 1, wherein the body has a square cross section.

\* \* \* \* \*